United States Patent [19]

Davis et al.

[11] Patent Number: 4,920,209

[45] Date of Patent: Apr. 24, 1990

[54] ORAL VACCINES

[75] Inventors: Alan R. Davis, Wayne; Paul P. Hung, Bryn Mawr, both of Pa.

[73] Assignee: American Home Products Corporation, New York, N.Y.

[21] Appl. No.: 58,002

[22] Filed: Jun. 4, 1987

Related U.S. Application Data

[63] Continuation-in-part of Ser. No. 782,638, Oct. 4, 1985, abandoned, which is a continuation-in-part of Ser. No. 667,233, Nov. 1, 1984, abandoned.

[51] Int. Cl.$^5$ .................... C12N 7/00; C12N 15/00; C12P 21/00
[52] U.S. Cl. .................... 435/235; 435/320; 435/172.3; 435/69.3; 424/89; 424/93
[58] Field of Search .................. 435/235, 68.91, 172.3, 435/320; 536/27; 935/57, 32, 34; 424/89, 93

[56] References Cited

PUBLICATIONS

Ellman et al., Nucleic Acid Research, vol. 11, pp. 4689–4701, 1983.
Laub et al., J. Virology, vol. 48, pp. 271–280, 1983.
Dyall-Smith et al., vol. 12, pp. 3973–3982, 1984.
Glugman et al., Eukaryobic Viral Vectors, Meeting date 1981, pp. 187–192.

*Primary Examiner*—Blondel Hazel
*Attorney, Agent, or Firm*—Robert Wiser

[57] ABSTRACT

Methods and vaccines for the production of antibodies to infectious organisms are described. Live recombinant adenovirus containing a foreign gene coding for an antigen produced by another infectious organism is delivered to the intestine of a warm-blooded animal in an enteric-coated dosage form, whereupon the virus infects the gut wall and induces the production of antibodies or cell mediated immunity to both adenovirus and the other infectious organism.

1 Claim, No Drawings

ORAL VACCINES

This application is a continuation-in-part of U.S. Ser. No. 782,638, filed Oct. 4, 1985, now abandoned, which is a continuation-in-part of U.S. Ser. No. 667,233, filed Nov. 1, 1984, now abandoned.

BACKGROUND OF THE INVENTION

A major goal of biomedical research is to provide protection against viral disease through immunization. One approach has been to use killed vaccines. However, large quantities of material are required for killed vaccinne in order to retain sufficient antigenic mass. In addition, killed vaccines are often contaminated with undesirable products during their preparation. Heterologous live vaccines, using appropriately engineered adenovirus, which is itself a vaccine, Chanock, R. M. et al., JAMA, 195, 151 (1966), seem an excellent immunogen. Out invention concerns live oral vaccines using adenovirus as vector.

Presently marketed adenovaccine comprises live, infectious adenoviruses in an enteric-coated dosage form. Upon administration to the patient to be vaccinated, the virus is carried past the upper-respiratory system (where disease-producing infection is thought to occur), and is released in the intestine. In the intestine, the virus reproduces in the gut wall, where, although it is not capable of causing adenoviral disease, nevertheless induces the formation of adenovirus antibodies, thus conferring immunity to adenoviral disease. In our invention, live, infectious adenovirus which has been engineered to contain genes coding for antigens produced by other disease-causing organisms is administered in an enteric-coated dosage form. Upon release in the intestine the virus will reproduce in the gut wall, will separately express both the adenoviral antigen and the pathogen surface antigen, and will induce the formation of antibodies or induce cell mediated immunity to both adenovirus and the other disease-causing organism. By "live virus" is meant, in contradistinction to "killed" virus, a virus which is, either by itself or in conjuction with additional genetic material, capable of producing identical progeny. By "infectious" is meant having the capability to deliver the viral genome into cells.

Approximately 200,000 persons in the United States are infected each year with Hepatitis B virus. In addition, there is a strong correlation between hepatitis B infection and liver cancer. The presently marketed vaccines against hepatitis B are injectable products manufactured from the blood plasma of healthy carriers by a lengthy process involving several discrete steps.

There are two major hepatitis B viral antigens: the surface antigen ($HB_sAg$) and the core antigen ($HB_cAg$). The antigenic structure of $HB_sAg$ is somewhat complex. There is a common group-specific determinant, a. In addition, there are two sets of mutually exclusive type-specific determinants d or y and w or r. The $HB_cAg$ is of a single antigenic type. It is known that production of antibody against $HB_sAg$ or $HB_cAg$ confers immunity against hepatitis B infection.

Several groups have employed recombinant DNA techniques to synthesize the $HB_sAg$ by microorganisms. $HB_sAg$ has been synthesized in *Escherichia coli* in the form of a fusion protein (Edman, J. C. et al., Nature, 291, 503 (1981)). It has also been synthesized in yeast using the ADH promoter (Valenzuela et al., Nature 298, 347 (1982)) of acid phosphatase promoter (Miyanohara et al., Proc. Natl. Acd. Sci. USA, 80, 1 (1983)). The expression of $HB_sAg$ by Adenovirus in eukaryotic cell strains has also been described (Perricaudet, et al., European Patent Publication 185,573 (1986)), as has the possibility of using adenoviruses modified at the E3 region by the insertion of recombinant DNA in the constitution of live vaccines (ibid, page 9). Finally, vaccinia virus has been used as a vector to produce a live virus vaccine to hepatitis virus (Smith et al., Nature, 302, 490 (1983)).

Rotaviruses are a major cause of acute gastroenteritis in infants. These viruses possess a genome of eleven double-stranded RNA segments enclosed in a capsid. The capsid contains an inner and outer shell. One of the outer shell proteins, VP7, is a glycoprotein that reacts with serotype-specific neutralizing antibodies (Kalica, A. R. et al., Virology, 112, 385 (1981)). This protein is coded for by gene 9 of the human type 1 (Wa) rotavirus. Gene 9 of type 1 human rotavirus has recently been cloned in *E. coli* and its sequence determined (Richardson, M. et al., J. Virol, 51, 860 (1984)).

Adenoviruses contain a linear duplex DNA molecule (m.w. $20 \times 10^6$–$25 \times 10^6$) that codes for 20-30 polypeptides. Many of these are incorporated into the viral particle which is morphologiclly complex and has a sophisticated assembly process. Previously SV40 T antigen has been expressed using an adenovirus recombinant (Solnick, D. Cell, 24, 135 (1981), Thummel, C. et al., Cell, 23, 825 (1981), Gluzman, Y. et al., in Eukaryotic Viral Vectors, p. 187, Cold Spring Harbor (1982)). Also mouse dihydrofolate reductase has been expressed using an adenovirus recombinant (Berkner, K. and Sharp, P. A., Nucleic Acids Research, 12, 1925 (1984)).

Roy, C., in European Patent Publication 80,806 (1983) proposes a method for producing immunity to microbial diseases by the administration of a microbe containing a foreign gene which will express an antigen of a second microbe to which immunity is desired. He states that preferred oral preparations are enteric-coated. Dulbecco proposes recombinant adenovirus vaccines in which the surface protein of adenovirus is modified to contain in its structure a segment of foreign protein which will produce a desired biological response on administration to animals (PCT International Publication Number WO 83/023 (1983)).

SUMMARY OF THE INVENTION

The invention sought to be patented in its method of treatment aspect comprises a method for producing antibodies or cell mediated immunity to an infectious organism in a warm-blooded animal which comprises orally administering to said warm-blooded animal, in an enteric coated dosage form, live recombinant adenoviruses in which the virion structural protein is unchanged from that in the native adenovirus from which the recombinant adenovirus is produced, and which contain the gene coding for the antigen corresponding to said antibodies or inducing said cell mediated immunity.

The invention sought to be patented in a subgeneric method of treatment aspect comprises a method for producing antibodies to hepatitis-B virus, rotavirus, or HIV in a warm-blooded animal which comprises orally administering to said warm-blooded animal live recombinant adenoviruses in which the virion structural protein is unchanged from that in the native adenovirus from which the recombinant adenovirus is produced, and which contain the gene coding for, respectively, a hepatitis-B antigen, a rotavirus antigen, or an HIV antigen.

The invention sought to be patented in its composition aspect comprises a vaccine for producing antibodies or cell mediated immunity to an infectious organism in warm-blooded animals comprising live recombinant adenoviruses in which the virion structural protin is unchanged from tht in the native adenovirus from which the recombinant adenovirus is produced, and which contain the gene coding for the antigen corresponding to said antibodies or inducing said cell mediated immunity, said vaccine being formulated in an enteric coated dosage form.

The invention sought to be patented in a subgeneric composition aspect comprises a vaccine for producing antibodies to hepatitis-B virus, rotavirus, or HIV in warm-blooded animals, comprising live recombinant adenoviruses in which the virion structural protein is unchanged from that in the native adenovirus from which the recombinant adenovirus is produced, and which contain the gene coding for, respectively, a hepatitis-B antigen, a rotavirus antigen, or an HIV antigen, said vaccine being formulated in an enteric-coated dosage form.

DETAILED DESCRIPTION OF THE INVENTION

Example 1

Adenovirus Vectors

Three adenovirus vectors (Gluzman, Y. et al., in Eukaryotic Viral Vectors p. 187, Cold Spring Harbor Laboratories, 1982) can easily be constructed. To maximize the length of foreign DNA that can be inserted, two expendable regions of the viral genome may be deleted, early regions 1 or early region 3 (E1 and E3), or both, of the adenovirus type 5 viral genome. ΔE1 is created by an in vivo recombinational event between a plasmid and a modified adenoviral DNA. (All plasmids described in this specification are propagated in *E. coil*). The plasmid is formed by insertion of adenoviral DNA sequences between 0 and 17 map units into pBR322 and subsequently, using restriction endonuclease digestion and ligation, deleting sequence between 1.4 and 9.1 map units and placing an Xbal restriction site at this junction. This plasmid is denoted in the art as pAC. The modified adenoviral DNA which contains a single Xbal restriction site at 4.0 map coordinates is formed as follows. Xbal cleaves wild type Ad5 DNA at four sites: 4, 29, 79, and 85 map units. Modified DNA lacking sites at 29, 79, and 85 is isolated by cutting Ad5 DNA with Xbal, transfecting the DNA and isolating the modified adenovirus which lacks Xbal sites at positions 29 and/or 79. This procedure is repeated again and modified adenovirus is isolated containing only the Xbal site at position 4. Such modified adenoviruses can also be readily constructed using techniques of oligonucleotide-directed mutagenesis (Smith, M., and Gillam, S. (1981) in Genetic Engineering, Setlow, J. K. and Hollaender, A., Eds. Vol. 3, pp. 1-32, Plenum, N.Y.). In this technique the Xbal restriction sites are destroyed using chemically synthesized oligonucleotides designed to produce silent changes in the amino acid coding regions defined by the respective Xbal restriction endonuclease sites. Vector ΔE3 is constructed by deletion of E3 region sequences. Two modified adenoviruses (type 5) are formed by the procedures outlined above. One contains no Xbal sites, the other contains only the Xbal sites at map coordinates 29, 79, and 85. The left half of DNA of the mutant containing no Xbal sites is joined with the right half of DNA of the mutant containing Xbal sites at 79 and 85, forming a modified adenovirus containing Xbal sites at only 79 and 85 map coordinates. Cleavage of this DNA with Xbal followed by religation forms the ΔE3 viral DNA deleting the E3 region between 79 and 85 map coordinates and placing a single Xbal cloning site at this junction. ΔE1ΔE3 may be constructed by deletions in both regions in a similar manner.

In a fashion similar to construction of ΔE1, ΔE3, and ΔE1ΔE3 vectors of adenovirus type 5, vectors of adenovirus types 4 and 7 are formed. For example, in adenovirus type 7, the E3 region is deleted between the Xbal site at 80.5 map coordinates and the EcoRl site at map coordinate 85.

Example 2

6X Series Plasmids. (For $Hb_sAg$ and rotavirus VP7)

Plasmids that allow the placement of the adenovirus 2 late promoter upstream from DNA coding for heptitis B surface antigen or rotavirus VP7 followed by SV40 splicing signals may be constructed. Each of these is flanked by Xbal sites for insertion into the adenovirus ΔE1, ΔE3, or ΔE1ΔE3 vectors.

a. p6XH.

Plasmid 6XH contains an Xbal linker at −400 bp of the Ad2 major late promoter and an EcoRl site at +33 bp, 8 bp before the end of the first adenovirus late leader. This is followed by an Eco RI linker at 26 bp preceding the ATG of $HB_sAg$ followed by $HB_sAg$ sequence of 678 bp to another Eco RI linker at 809 bp. This is followed by SV40 sequence extending from 2753-2516 bp on the SV40 map. These sequences are all inserted into the large pBR322 Bam HI to Eco RI fragment via Xbal linkers.

b. p6XR.

Plasmid p6XR is made by joining the rotavirus VP7 gene with Eco RI linkers at nucleotide 6 and 1036 to the Ad2 major late promoter containing an Xbal site at −400 bp and an Eco Rl linker at +331 and attaching SV40 sequences from 2753-2516 behind the VP7 gene with an Eco Rl linker at 2753 (SV40 map coordinate) and an Xbal site at 2516 bp. This cassette is inserted into the large Eco Rl to BamH fragment of pBR322.

c. Transfer of plasmid sequences to the viral DNA vector and production of recombinant adenovirus.

The transfer of the cassette of promoter-foreign gene-terminator to the adenovirus vector is done either as follows or by in vivo recombination (see detailed example below). The purified adenovirus vector DNA is cleaved with a restriction endonucleose followed by treatment with calf intestine alkaline phosphatase to prevent self ligation. Plasmid derived sequences are obtained by cleavage of p6XH of p6XR with Xbal. These are then ligated to the adenoviral vector DNA. Either 293 cells, (Graham, et al., Gen. Virol., 86 10 (1978)), Hela cells, or Wi-38 cells are then transfected with the ligation mixture and overlayed with agar. Plaques are picked 7-10 days later and viral stocks prepared.

Example 3

Expression Assays

Three types of assays have been used to assess expression of hepatitis B surface antigen and rotavirus VP7. These are:

a. Indirect immunofluorescence.

Either mouse monoclonal antibodies or rabbit antisera are used to detect expression of recombinant ΔE1 and ΔE3 virus stocks containing $HB_sAg$ or VP7 DNA sequences. Counterstaining is with goat anti-mouse or anti-rabbit FITC.

b. Immunoprecipitation.

Immunoprecipitation of $HB_sAg$ or rotavirus VP7 in cells infected with the recombinant adenovirus is done using either mouse monoclonal antibodies or rabbit polyclonal antisera against $HB_sAg$ or rotavirus VP7 and protein A Sepharose CL4B.

c. RIA.

Expression of $HB_sAg$ is also tested by a commercially available radioimmunoassay (Ausria, Abbott Labs.).

Example 4

Immunogenic Nature of the Recombinant Adenovirus

Live, lyophilized recombinant adenovirus contained in an enteric coated capsule is assessed for immunogenicity by giving them ($10^4$–$10^5$ 50% infectious dose/tablet) to hamsters or chimpanzees and testing for antibody levels and protection from challenge.

The presently marketed adenovirus vaccine contains living lyophillized adenovirus of either of type 4 or type 7 mixed with inert ingredients prepared in enteric coated tablets. Administration of tablets (approximately $10^4$ $TCID_{50}$ of virus) results in selective gastrointestinal infection without illness. The vaccine is safe; the induced infection is specifically restricted to the intestinal tract, and the vaccine virus is not transmitted from vaccinees to susceptible close contacts. Specific neutralizing antibody is noted in over 95% of vaccinated individuals 21 days after immunization. The new vaccines of the present invention which are specifically described are comprised of recombinant adenoviruses expressing hepatitis B surface antigen and rotavirus VP7 and are formulated and work in the same fashion as the present adenovirus vaccine except that antibody to hepatitis B surface antigen or rotavirus VP7 is produced as well as antibody to adenovirus. In any of the embodiments of the invention, the administration of approximately $10^4$ $TCID_{50}$ of recombinant virus, or even considerably less, will, of course, produce the desired immunogenic response. The determination of the optimum dosage will vary depending on the particular recombinant adenovirus employed; determination of this optimum is within the skill of the art.

Example 5

Detailed example of a recombinant that expresses authentic $HB_sAg$

As a detailed example of the construction of one adenovirus recombinant, the $HB_sAg$ gene of the adw subtype from 26 bp upstream of the $HB_sAg$ translation initiation codon and 131 bp downstream from the translation termination codon was flanked by upstream sequences from the Ad2 major late promoter (+33 to 400 bp; Solnick, D., Cell, 24, 135–143 (1981) and by downstream sequences from SV40 (2753 to 2516 bp; Tooze, J. (Ed.) Molecular Biology of Tumor Viruses, Cold Spring Harbor Laboratory pp. 801–829 (1980)). This plasmid is termed p6XH (see above). These sequences were inserted into the unique Xbal site plasmid pAC that contains an insert of Ad5 DNA extending from the Eco RI linker at the left end of the adenovirus genome to the Hind III site at Ad5 map coordinate 17.0 (Gluzman, U., Reichl, H., and Solnick, D., 1982, in (Y. Gluzman, Ed.) Eukaryotic Viral Vectors, Cold Spring Harbor Laboratories, p. 187–192). The new plasmids (pACH-2 and pACH-9) with the cassette containing the Ad2 major late promoter—$HB_sAg$ gene—SV40 processing signals in either orientation, were cleaved with Hind III. The Hind III cleavage product of each was combined with the large Xbal fragment of the adenovirus mutant ΔE1 extending from map coordinates 9.1 to 100 (Gluzman, Y., Reichl, H., and Solnick, D., 1982 in (Y. Gluzman, ed.) Eukaryotic Viral Vectors, Cold Spring Harbor Laboratories, pp. 187–192). This DNA mixture was transfected (Graham, F. L. and ven der Eb, A. J. Virology 52, 456–467 (1973)) onto 293 cells (Graham, F. L., Smiley, J., Russell, W. C., and Nairn, R., J. Gen. Virol., 36, 59–72 (1977)) and cells were overlaid with agar for plaque detection. Approximately 10–14 days later, 54 plaques were picked and virus stocks generated from each. These viruses were screened for the presence of $HB_sAg$ DNA by hybridization to a $^{32}P$-labeled $HB_sAg$ DNA probe. Positive plaques (49 out of 54) were next infected onto monolayers of 293 cells and the expression of authentic $HB_sAg$ was detected in cell lysates by both radioimmunoassay (AUSRIA, Abbott Laboratories, Inc. or NML-$HB_sAg$ RIA, Nuclear-Medical Laboratories) and by immunoprecipitation of $^{35}S$-radiolabeled $HB_sAg$ using a monoclonal antibody to $HB_sAg$ (anti-a subtype, Boehringer Mannheim Biochemicals).

In the specific example above, we use the Ad2 major late promoter extending only 33 nucleotides downstream from the transcriptional initiation site so that the first splice site is not included. This promoter contains only the first part of the tripartite leader of the adenoviral major late promoter. However, the major late promoter from other adenoviruses particularly types 3, 4, 5, or 7 can be used and the full tripartite leader of this promoter can be used. In the following example we describe the construction of two bacterial plasmids, pHM1 and pHM2 which contain cassettes composed of the Ad2 major late promoter and the leftmost 168 bp of the 200 bp Ad2 tripartite leader followed by the $HB_sAg$ gene and processing and polyadenylation signals from SV40 virus. These plasmids also contain adenovirus sequences flanking the cassette so that homologous recombination can be used to insert the cassette into the adenoviral genome. On the left the cassette is flanked by the leftmost 353 bp of the Ad5 genome and on the right by map coordinates 8–15.5 of adenovirus 5. Plasmid pHM1 contains 19 bp of SV40 virus sequence (Sv40 nucleotides 5173–5174) preceding the $HB_sAg$ gene. Plasmid pHM2 is identical to pHM1 except that it does not contain this sequence.

The cassettes from both pHM1 and pHM2 were placed a the E1 region of the adenovirus 5 genome by the technique of homologous recombination as described above. Each plasmid was linearized and combined with the large Xbal fragment of the adenovirus mutant ΔE1 extending from map coordinates 9.1 to 100 (Gluzman, Y., Reichl, H. Solnick, D., 1982 in (Y. Gluzman, ed.) Eukaryotic Viral Vectors, Cold Spring Harbor Laboratories, pp. 187-192). Plaques were picked and stock viruses generated from each.

When these stock viruses (HM1 and HM2) were infected on a human embryonic kidney (293) cell line (Graham, F. L., Smiley, H., Russell, W. C. and Nairn, R. (1977) J. Gen. Virol. 36, 59-72) we found, after 40 h infection, approximately 1 μg $HB_sAg$ (based upon radioimmunoassay and comparison of cpm to $NML-HB_sAg$ kit positive control) per $5 \times 10^6$ infected cells were observed in culture supernatants of HM2 infected cells. HM1 virus yielded approximately 60% of this amount. We found that the $HB_sAg$ polypeptides produced by these viruses were glycosylated (P2) and nonglycosylated (P1) forms (Marions, P.L., Salazar, F. H., Alexander, J. J. and Robinson, W. (1979) J. Virol. 32, 796-802; Peterson D. L. (1981) J. Biol. Chem. 256, 6975-6983). At 40 h after infection most of the $HB_sAg$ (78%) was secreted from cells into the culture medium as a particle (density = 1.20 g/ml) the same or nearly the same as the 22 nm particle (Gerin, J. L., Purcell, R. H., Hoggan, M. D., Holland, P. V. and Chanock, R. M. (1969) J. Virol. 4, 763-768; Gerin, J. L., Holland, P. V., and Purcell, R. H. (1971) J. Virol. 7, 569-576) observed in human serum. HM2 yielded approximately 40% more $HB_sAg$ than HM1. However, when MH2 was compared to the previously described hybrid adenovirus, ΔE1H, a 70-fold increase in $HB_sAg$ polypeptide was noted by HM2 virus.

Instead of the adenoviral major late promoter, any other suitable eukaryotic promoter can be used, such as human metallothionein promoter or the human dihydrofolate reductase promoter. In addition, in our examples, we have used adenovirus type 5 DNA as vector for foreign gene expression; however, other adenovirus types can be used as vector, and particularly useful are types 3, 4, and 7 that are presently in use as vaccines.

Also, we describe the use of processing and polyadenylation signals from SV40 DNA; however, any suitable processing and polyadenylation signals may be used. These may come from adenoviral DNA, particularly types 3, 4, and 7.

Example 6

Recombinant Adenovirus AD7HZ6-1

Example of a recombinant adenovirus type 7, Ad7HZ6-1, that contains hepatitis B virus DNA inserted into the E3 region of the adenovirus genome and that replicates in human cells, directing the expression of hepatitis B virus surface antigen.

Ad7HZ6-1 was assembled by transfecting A549 cells (ATCC CCL 185) with overlapping viral DNA fragments that recombined in vivo to generate a complete recombinant viral genome capable of replicating and of producing infectious recombinant adenovirus (Davis, A. R., et al., [1985] Proc. Natl. Acad. Sci. USA 82, 7560-7564). The majority of the recombinant viral genome was derived from the Eco RI "A" genomic fragment of adenovirus type 7 (strain 55142) DNA that extends from map unit 0 to map unit 87. The other viral DNA fragment was a cloned, recombinant fragment that extends from map unit 68 to map unit 100 and contains the hepatitis B virus DNA; it was constructed as described below by standard techniques of molecular biology (Maniatis, T., et al., [1982] Molecular Cloning: A Laboratory Manual, Cold Spring Harbor Laboratory, Cold Spring Harbor, NY).

Adenovirus type 7 (strain 55142) DNA was cloned into the Eco RI site of pBR322 (Pharmacia Inc., Piscataway, NH) as described (Hanahan, D. and Gluzman, Y. [1984] Molecular and Cellular Biology 4, 302-309). This procedure yielded recombinant plasmid WypAd7RIA-17 which contains adenovirus viral DNA between map unit 0 and map unit 87 with some deletions between map unit 40 and map unit 65. Recombinant plasmid WpyAd7RIB-10 that contains the Eco Ri "B" fragment which extends from map unit 87 to map unit 100 was also recovered. Portions of these two plasmids were combined to create a plasmid that contains adenovirus DNA between map unit 68 and map unit 100 except that the Hind III "H" fragment (map units 80-84) is replaced by a chemically synthesized polylinker region.

WypAd7RIA-17 was digested with Sal I and religated to make ChpAd717E27w.t. which lacks the Sal I "A" fragment (map units 18-68). ChpAd717E27w.t. was digested with Eco RV, Sal I and Hind III. Three of the resulant fragments, pBR322 between the Eco RV site and the Sal I site, adenovirus between map unit 68 (Sal I) and map unit 80 (Hind III), and the recombinant fragment containing adenovirus between map unit 84 (Hind III) and map unit 87 (Eco RI) joined to pBR322 from the Eco RI site to the Eco RV site, were separated by gel electrophoresis, purified and ligated together in the presence of a synthetic polylinker (Pharmacia Inc., Piscataway, NJ) with Hind III ends and an internal Xba I site. The plasmid ChpAd717E27HΔ was recovered from this ligation and digested with Sal I and Eco RI to obtain a cloned adenoviral DNA fragment extending from map unit 68 to map unit 87, with the Hind III "H" fragment replaced by a synethetic polylinker.

The Eco RI site added to the terminus of the viral genome at map unit 100 during cloning was replaced by a Sal I site in the following steps. WypAd7RIB-10 was digested with Eco RI, the Eco RI sites were filled-in with Klenow DNA polymerase, Sal I linkers were ligated to the filled-in ends, followed by digestion with Sal I and Bam HI. The adenoviral DNA fragment extending from the Bam HI site at map unit 92.5 to the synthetic Sal I site at map unit 100 was cloned into pUC19 (Pharmacia Inc., Piscataway, NJ). An adenoviral DNA fragment extending from map unit 87 (Eco RI) to map unit 92.5 (Bam HI) was prepared from WypAd7RIB-10 and added to this pUC19 recombinant to make ChpAd73'RS.1. ChpAd73'Rs.1 was digested with Eco RI and Sal I to obtain a cloned adenoviral DNA fragment extending from map unit 87 (Eco RI) to map unit 100 (Sal I).

The cloned adenoviral DNA fragment extending from map unit 68 to map unit 87 obtained from ChpAd717E27HΔ and the cloned adenoviral DNA fragment extending from map unit 87 to map unit 100 obtained from Chp Ad73'RS.1 were ligated together and then inserted into the Sal I site of pBR328 (Soberon, X., et al., [1980] Gene 9, 287-305) to create ChpAd7-SalBHΔ.

Hepatitis B virus DNA was obtained from a plasmid that contains hepatitis B virus genome cloned at the Eco RI sites. The numbering of the nucleotides in this hepatitis B virus genome is identical to that of Ono et al., [1983] Nucleic Acids Res., 11, 1747-1757. The fragment of the hepatitis B virus genome that contains the genetic code for hepatitis B virus major surface antigen, the major envelope protein, lies between an FnuD II site at nucleotide 131 and a Hpa I site at nucleotide 966. This DNA fragment was excised by digestion with FnuD II and Hpa I, Sal I linkers were added, and it was cloned into a pBR322 derivative to create the plasmid, pHMHS.3C. Hepatitis B virus DNA clones are readily available, for example ATCC 45020 from the American Type Culture Collection.

The DNA fragment that contains the genetic code for the hepatitis B virus major surface angtigen was obtained from pHMHS.3C by Sal I digestion, the terminii were filled-in with Klenow DNA polymerase and Nhe I linkers were added, followed by Nhe I digestion. This fragment was inserted into the unique Xba I site of ChpAd7SalBHΔ, between adenovirus map unit 80 and map unit 84, to create pCAd7ΔHS1-5. in pCAd7ΔHS1-5, the hepatitis DNA fragment that contains the genetic code for the hepatitis B virus major surface antigen is oriented so that the translation initiation codon is proximal to the putative adenovirus E3 region promoter. Digestion of the Cla I site in the pBR328 portion yielded linear pCAd7 HS1-5; this cloned, recombinant viral DNA fragment extending from map unit 68 to map unit 100 was cotransfected into A549 cells with the Eco RI "A" genomic DNA fragment to generate the novel recombinant adenovirus Ad7HZ6-1.

Within 8 to 14 days after transfection, recombinant viruses were recovered as plaques on the A549 cell sheet. These viruses were screened for their ability to direct the production of hepatitis B virus major surface antigen in infected A549 cells by radioimmunoassay (Organon Teknika Corp., Irving, TX). After several rounds of plaque purification, Ad7HZ6-1 was amplified to high titer and genomic DNA was prepared and mapped with restriction endonucleases. This analysis confirmed the expected structure. A549 cells infected with Ad7HZ6-1 secreted approximately 1 μg of immunoreactive hepatitis B virus major surface antigen per 5 million cells within 48 hours (this corresponded to approximately 40,000 cpm per 100 μl sample of tissue culture supernatant using the radioimmunoassay). Ad7HZ6-1 has been deposited with the American Type Culute Collection and has been designated ATCC VR2167.

In practicing the method of this invention, where the foreign gene is inserted in deleted early region 3 of the adenovirus, the recombinant virus remains infective, and the vaccination requires nothing more than delivery of the recombinant virus to the gut. On the other hand, early region 1 is essential to adenovirus infectivity. Therefore, if the foreign gene is inserted in deleted early region 1, helper virus must be co-administered. This helper virus is conveniently unmodified, infectious adenovirus. Also, the helper virus can itself be a defective virus with a deletion which can be complemented by the recombinant virus. In this fashion virus growth and foreign antigen production would be elicited only in cells infected with both viruses. This defective helper virus can be of the same or of different subtype as the recombinant virus. If differing subtype (e.g. if recombinant virus was Ad4 subtype and the defective virus of Ad7 subtype), formation of wild type virus though recombination should be minimized. Propagation of virus for vaccine production can be accomplished either through co-cultivation of both viruses in human diploid fibroblasts or cultivation of viruses separately in cell lines known to complement each of the defects.

In addition to the E1 and E3 regions, there are several other regions of the viral genome where the cassette containing promoter, tripartite leader, foreign gene, and processing and polyadenylation signals may be inserted. These include a region between E1a and E1b, regions at the left and right ends of the genome, and at the E4 region, and between L5 and E4 regions. Some examples are given below:

Ad5 contains an E1a promoter at map coordinate 1.4 and an E1b promoter at map coordinate 4.7. The polyadenylation site for E1a is at map coordinate 4.6, nucleotide 1631, at nucleotide 1671 is the TATA box for the E1b promoter. At nucleotide 1572 there is a unique Hpal site (GTTAAC). This site can be utilized for placement of the adenovirus type 2 major late promoter and hepatitis B surface antigen and use of the E1a polyadenylation site. Polyadenylation of E1a can be provided by placement of a polyadenylation signal from SV40 viral DNA behind E1a or from the L4 region of the virus. The additional DNA in the genome in the above construct may be compensated by removal of DNA determined non-essential in the E3 region.

Other insertion points are the extreme left and right ends of the genome. At the left end of the position will be between the 116 bp inverted terminal repeat and the TATA box of the E4 promoter. In Ad2 there is an Mbo II site at 99.3 map units. This is 191 bp from the extreme right end of the viral DNA. In Ad5 there is a ThaI (FnU4DII) site 240 bp from the left end of the genome. This region is between the ITR and upstream of the E4 TATA box. Again, if necessary, insertion will be made into an E3 deletion mutant to accommodate the extra DNA.

In each case these regions can be used as insertion points for the cassette of the adenovirus major late promoter, adenovirus tripartite leader, foreign gene and processing and polyadenylation signals in adenovirus type 4 and type 7 strains that are used for the presently marketed adenovirus vaccines.

Although the foregoing specification specifically refers to adenovirus of types 4, 5, or 7, live, infectious adenovirus of any type may be employed in this invention. Adenovirus of types 4 or 7 are preferred since these are the types presently employed in commercial adenovirus vaccines. Similarly, although specific reference has been made to vaccines producing antibodies to hepatitis-B, rotavirus, and HIV, our invention provides oral vaccines against any infectious agent containing an antigen to which a warm-blooded animal will produce antibodies or cell mediated immunity, and which antigen is coded for by a gene composed of up to about 3000 base pairs. Thus, for example, included within the scope of the invention are immunization against such diseases as influenza, parainfluenze, respiratory synctial virus disease, hepatitis A, acquired immunodeficiency syndrome (AIDS), cholera, E. coli, pertussis, diphtheria, tetanus, shigellosis, gonorrhea, mycoplasma pneumonia, and so on.

What is claimed is:

1. A recombinant adenovirus containing a gene coding for an antigen produced by a disease-causing organism said recombinant adenovirus being of type 7; the gene codes for hepatitis-B surface antigen; and the gene is located at delected early region 3; said recombinant adenovirus being ATCC VR2167.

* * * * *